US007264923B2

(12) United States Patent
Virgin et al.

(10) Patent No.: US 7,264,923 B2
(45) Date of Patent: Sep. 4, 2007

(54) NOROVIRUS INFECTED CELL CULTURES AND USES THEREFOR

(75) Inventors: Herbert W. Virgin, St. Louis, MO (US); Christiane Wobus, Kirkwood, MO (US); Stephanie Karst, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 10/839,211

(22) Filed: May 5, 2004

(65) Prior Publication Data

US 2005/0255480 A1 Nov. 17, 2005

(51) Int. Cl.
 C12Q 1/70 (2006.01)
 C12N 5/00 (2006.01)
 C12N 5/02 (2006.01)
 C12N 7/00 (2006.01)
 C12N 7/02 (2006.01)
 C12N 5/06 (2006.01)
 C12P 21/04 (2006.01)

(52) U.S. Cl. ............... 435/5; 435/325; 435/235.1; 435/239; 435/354; 435/7.21; 435/70.3

(58) Field of Classification Search .............. 435/5, 435/325, 235.1, 41, 91.33
 See application file for complete search history.

(56) References Cited

U.S. PATENT DOCUMENTS 5,198,428 A 3/1993 Sivaramakrishnan et al.

OTHER PUBLICATIONS

Duizer et al., Laboratory efforts to cultivate norovirus, Journal of General Virology, 2004, vol. 85, p. 79-87.*
Akagawa et al., "Generation of CD1 +RelB+ Dendritic Cells and Tartrate-Resistant Acid Phosphatase-Positive Osteoclast-Like Multinucleated Giant Cells from Human Monocytes," Blood, 1996, pp. 4029-4039, vol. 88.
Atmar et al., "Diagnosis of Noncultivatable Gastroenteritis Viruses, the Human Caliciviruses," Clinical Microbiology Reviews, 2001, pp. 15-37, vol. 14.
Darnell et al., "Jak-STAT Pathways and Transcriptional Activation in Response to IFNs and Other Extracellular Signaling Proteins," Science, 1994, pp. 1415-1421, vol. 264.
Dieu et al., "Selective Recruitment of Immature and Mature Dendritic Cells by Distinct Chemokines Expressed in Different Anatomic Sites," J. Exp. Med., 1988, pp. 373-386, vol. 188.
Duizer et al., "Laboratory Efforts to Cultivate Noroviruses," J. Gen. Virol., 2004, pp. 79-87, vol. 85.
Herbst et al., "CD34+ Peripheral Blood Progenitor Cell and Monocyte Derived Dendritic Cells: A Comparative Analysis," Br. J. Haematol., 1997, pp. 490-499, vol. 99.
Heise et al., "Murine Cytomegalovirus Infection Inhibits IFNγ-Induced MHC Class II Expression on Macrophages: The Role of Type I Interferon," Virology, 1998, pp. 331-344, vol. 241.
Hovanessian, "Interferon-Induced dsRNA-Activated Protein Kinase (PKR): Antiporliferative, Antiviral and Antitumoral Functions," Semin. Virol., 1993, pp. 237-245, vol. 4.
Hwang et al., "Evidence of a Pluripotent Human Embryonic Stem Cell Line Derived from a Cloned Blastocyst," Science, 2004, pp. 1669-1674, vol. 303.
Inaba et al., "Generation of Large Numbers of Dendritic Cells from Mouse Bone Marrow Cultures Supplemented with Granulocyte/ Macrophage Colony-Stimulating Factor," Exp. Med., 1992, pp. 1693-1702, vol. 176.
Jaffe, "Review of Human Dendritic Cells: Isolation and Culture from Precursors," Pediatr. Pathol., 1993, pp. 821-837, vol. 13.
Karst et al., "STAT1-Dependent Innate Immunity to a Norwalk-Like Virus," Science, 2003, pp. 1575-1578, vol. 299.
Keller et al., "Hematopoietic Commitment During Embryonic Stem Cell Differentiation in Culture," Mol. Cell. Biol., 1993, pp. 473-486, vol. 13.
Langloss et al., "In Vitro Interaction of Alveolar Macrophages and Pneumocytes with Feline Respiratory Viruses," Infection Immun., 1978, pp. 836-841, vol. 20.
Lee et al., "Generation of Macrophages from Early T Progenitors in vitro," J. Immunol., 2001, pp. 5964-5969, vol. 166.
Macmicking et al., "Altered Responses to Bacterial Infection and Endotoxic Shock in Mice Lacking Inducible Nitric Oxide Synthase," Cell, 1995, pp. 641-650, vol. 81.
Mitchell et al., "Dendritic Cell/Macrophage Precursors Capture Exogenous Antigen for MHC Class I Presentation by Dentritic Cells," Eur. J. Immunol., 1998, pp. 1923-1933, vol. 28.
Miyamoto et al., "Bifurcation of Osteoclasts and Dendritic Cells from Common Progenitors," Blood, 2001, pp. 2544-2554, vol. 98.
Müller et al., "Functional Role of Type I and Type II Interferons in Antiviral Defense," Science, 1994, pp. 1918-1921, vol. 264.
National Center For Research Resources, "Research Highlights—Escaping the Norwalk Virus," http://www.ncrr.nih.gov/newspub/oct03rpt/stories2.asp, 2004, 3 pages.
Pollock et al., "Latent Murine Cytomegalovirus Infection in Macrophages," Virology, 1997, pp. 168-179, vol. 227.

(Continued)

Primary Examiner—Bruce R. Campell
Assistant Examiner—Sharon Hurt
(74) Attorney, Agent, or Firm—Sonnenschein Nath & Rosenthal LLP

(57) ABSTRACT

A norovirus-permissive cell culture infected with a norovirus, and methods of culturing a norovirus, are disclosed. Norovirus-permissive cells include dendritic cell-lineage cells, and macrophage-lineage cells, such as dendritic cells, and macrophages having a deficiency in a cellular anti-viral pathway such as a STAT-1-dependent pathway, an interferon receptor-dependent pathway, or a PKR-dependent pathway. Also disclosed are methods of screening anti-viral compounds against norovirus-permissive cells infected with norovirus, and norovirus adapted to grow in fibroblasts as well as macrophages that are not deficient in a cellular anti-viral pathway. Methods of making a norovirus vaccine are also disclosed.

14 Claims, 6 Drawing Sheets

OTHER PUBLICATIONS

Figure 1:
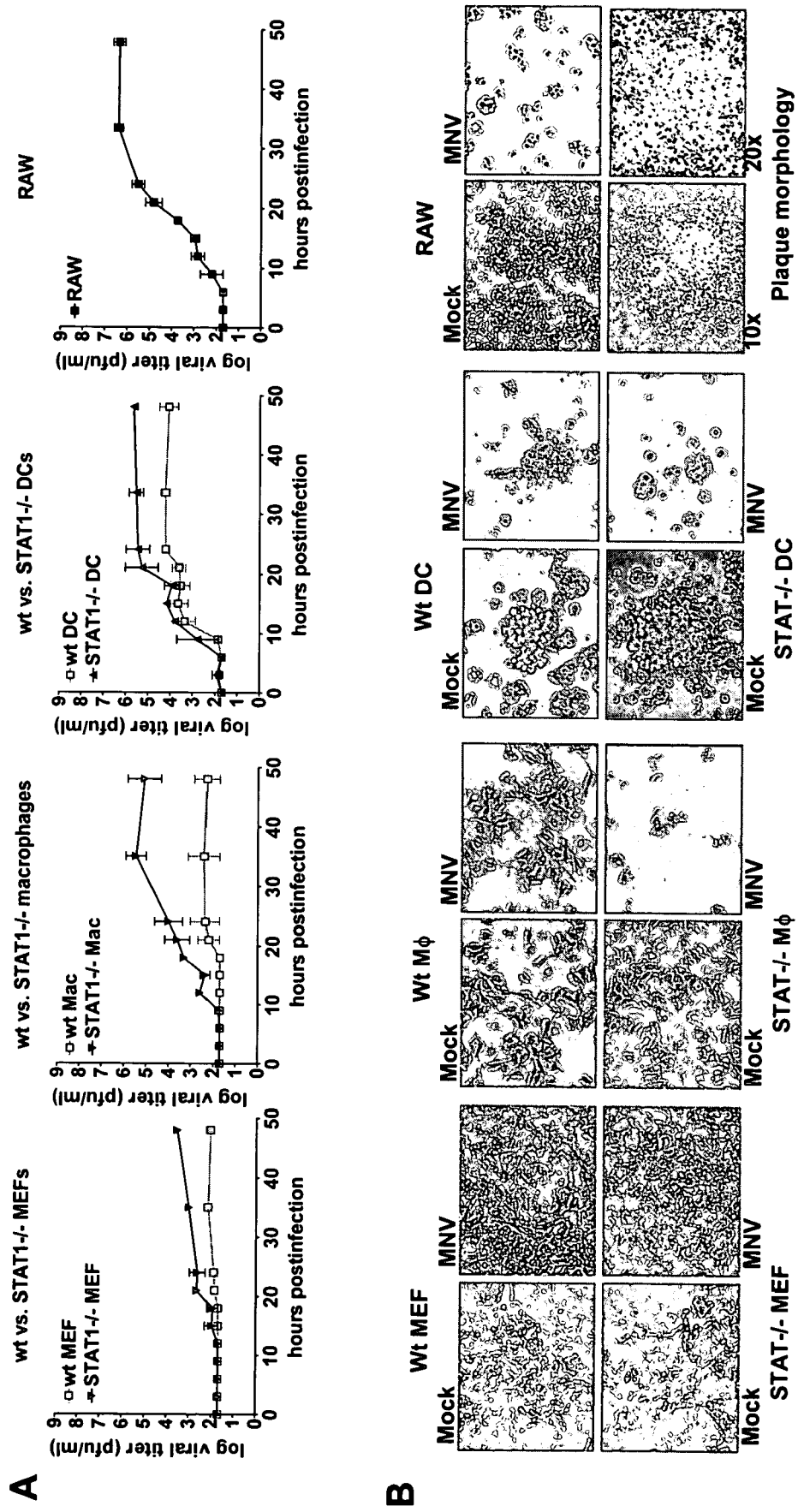

Ralph et al., "Lysozyme Synthesis by Established Human and Murine Histiocytic Lymphoma Cell Lines," J. Exp. Med., 1976, pp. 1528-1533, vol. 143.

Reckess, "New Mouse Virus may Help Scientists Better Understand Cruise Ship Epidemics," http://mednews.wustl.edu/medadmin/PAnews.nsf/PrintView/AE60E8F4D53C2B8C86256CE0005DBB1, 2004, 2 pages.

Sabin, "Characteristics and Genetic Potentialities of Experimentally Produced and Naturally Occurring Variants of Poliomyelitis Virus," Ann. N.Y. Acad. Sci., 1955, pp. 924-938, vol. 61.

Sapi, "The Role of CSF-1 in Normal Physiology of Mammary Gland and Breast Cancer: An Update," Exp. Biol. Med., 2004, pp. 1-11, vol. 229.

Seal et al., "Isolation of Caliciviruses from Skunks That are Antigenically and Genotypically Related to San Miguel Sea Lion Virus," Virus Res., 1995, pp. 1-12, vol. 37.

Senju et al., "Generation and Genetic Modification of Dendritic Cells Derived from Mouse Embryonic Stem Cells," Blood, 2003, pp. 3501-3508, vol. 101.

Stuart et al., "Differential Induction of Bone Marrow Macrophage Proliferation by Mycoplasmas Involves Granulocyte-Macrophage Colony-Stimulating Factor," Infection Immun., 1990, pp. 3558-3563, vol. 58.

Wiles et al., "Multiple Hematopoietic Lineages Develop from Embryonic Stem (ES) Cells in Culture," Development, 1991, pp. 259-267, vol. 111.

Wobus et al., "Replication of *Norovirus* in Cell Culture Reveals a Tropism for Dendritic Cells and Macrophages," PLOS Biology, 2004, pp. 2076-2084, vol. 2.

Yang et al., "Deficient Signaling in Mice Devoid of Double-Stranded RNA-Dependent Protein Kinase," EMBO J., 1995, pp. 6095-6106, vol. 14.

\* cited by examiner

NOROVIRUS INFECTED CELL CULTURES AND USES THEREFOR

GOVERNMENT INTERESTS

This work was supported at least in part with funds from the federal government under U.S.P.H.S. Grant RO1 AI54483, awarded by the National Institutes of Health. The U.S. Government may have certain rights in the invention.

FIELD

This invention relates generally to the field of virology, and, more particularly, to methods and uses for norovirus culture.

BACKGROUND

Norovirus, which is a single-stranded, positive strand RNA virus belonging to the family calciviridae, causes over 90% of non-bacterial epidemic gastroenteritis worldwide. However, norovirus has been poorly understood because of a lack of a cell culture system supporting norovirus replication (Atmar, R. L. and Estes, M. K., Clinical Microbiology Reviews 14: 15-37, 2001). Norovirus, including human forms of norovirus (i.e., Norwalk virus), can be detected in diagnostic or clinical samples such as stool specimens or vomitus of diseased individuals. Norovirus can also be present in body tissues, such as brain tissue, in an infected mammalian organism. Previous attempts to culture norovirus have been unsuccessful (reviewed in Duizer E, et al. J Gen Virol. 85(Pt 1): 79-87, 2004). There is thus a need to establish a norovirus culture system.

SUMMARY

Accordingly, the present inventors have succeeded in discovering methods for culturing norovirus and in developing norovirus-permissive host cells. The culture methods can be used for a variety of purposes, such as diagnostic methods, development of assays for viral replication, selection of mutant viruses with desirable properties, screening of potential anti-viral compounds, and development of vaccines.

Thus, in various embodiments, the present invention can comprise a norovirus-permissive cell culture infected with a norovirus. Such norovirus-permissive cell cultures can be comprised of vertebrate cells, in particular haematopoietic cells such as macrophage-lineage cells and dendritic cell-lineage cells (DC-lineage cells). The macrophage-lineage cells can be, for example, bone marrow macrophages, umbilical cord macrophages, peripheral blood mononuclear cells, human leukocyte/mouse macrophage hybrid cells and embryonic stem cell macrophages.

In certain embodiments, the macrophages that can support norovirus replication can be macrophages deficient in one or more anti-viral pathways. The deficiency in a cellular anti-viral pathway can be a deficiency in a STAT-1-dependent anti-viral pathway (Darnell, J. E. et al., Science 264: 1415-1421, 1994) a deficiency in an interferon receptor-dependent anti-viral pathway, a deficiency in a double-stranded RNA-dependent serine/threonine protein kinase (PKR)-dependent anti-viral pathway (Hovanessian, A. G. Semin. Virol. 4, 237-245, 1993), or combinations thereof. Accordingly, macrophages which can support norovirus replication can be STAT-1-deficient macrophages, PKR-deficient macrophages, or interferon receptor-deficient macrophages. The interferon receptor deficient macrophages can be deficient in an interferon-αβ receptor, deficient in an interferon-γ receptor, deficient in an interferon λ receptor, or a combination thereof. Macrophages deficient in the PKR-dependent anti-viral pathway can be macrophages deficient in PKR.

In certain configurations, the macrophage lineage cells can be transformed macrophages. In some aspects, transformed macrophages can be established macrophage cell lines such as RAW 264.7 cells, J774A.1 cells or WBC264-9C cells (a human leukocyte/mouse macrophage hybrid cell line).

In certain configurations, the dendritic cell lineage cells can be bone marrow dendritic cells, peripheral blood dendritic cells, or transformed dendritic cells.

In some embodiments, the vertebrate cells can be murine cells, while in other embodiments, the vertebrate cells can be human cells or hybrid cells such as human-mouse fusion cells. In some configurations, a norovirus can be a murine norovirus, while in other configurations, a norovirus can be a human norovirus.

In various embodiments, the present invention can involve methods of replicating a norovirus in vitro. The methods can comprise inoculating norovirus-permissive cells with a norovirus, and culturing the cells. In these embodiments, inoculating norovirus-permissive cells can comprise infecting the cells with the norovirus, or transfecting the norovirus-permissive cells with a nucleic acid comprising a norovirus genome or a portion thereof comprising at least 25 nucleotides. In various configurations, the methods can comprise inoculating vertebrate cells which can be macrophage-lineage cells or dendritic cell-lineage cells. The macrophage-lineage cells which can be inoculated can be macrophage-lineage cells deficient in a cellular anti-viral pathway such as a STAT-1-dependent anti-viral pathway, an interferon receptor-dependent anti-viral pathway, a PKR-dependent anti-viral pathway, or a combination thereof. The macrophages deficient in an interferon-dependent pathway which can be inoculated can be deficient in an interferon-αβ receptor, an interferon-γ receptor, an interferon λ receptor or a combination thereof. The macrophages deficient in the PKR-dependent pathway which can be inoculated can be PKR-deficient macrophages. In some configurations, the macrophage-lineage cells which can be inoculated can be transformed macrophages such as RAW 264.7 cells, J774A.1 cells or WBC264-9C cells. In certain configurations, the norovirus-permissive cells which can be inoculated with norovirus can be dendritic cells such as bone marrow dendritic cells, peripheral blood dendritic cells, and transformed dendritic cells. In various embodiments of the invention, the cells that can be inoculated with norovirus can be vertebrate cells such as human cells, murine cells, or human-murine fusion cells, and the norovirus can be a murine norovirus or a human norovirus such as a Norwalk virus.

In various embodiments, the invention comprises methods of detecting norovirus in a biological sample. In one aspect, such methods can involve contacting a cell culture comprising norovirus-permissive cells with the sample, and detecting norovirus viral replication in the cell culture. The sample in some configurations can be a diagnostic sample, such as a diagnostic sample from a mammal suspected of infection with the norovirus. The mammal can be a human, a laboratory animal such as a rodent, a farm animal, or a companion animal. The diagnostic sample can be a tissue sample, a blood sample, a vomitus sample, a sputum sample or a stool sample. The norovirus-permissive cells in these embodiments can be dendritic cell-lineage cells or macrophage-lineage cells. The macrophage-lineage cells can be macrophages deficient in a cellular anti-viral pathway such a STAT-1-dependent anti-viral pathway, an interferon receptor-dependent anti-viral pathway, a PKR-dependent anti-viral pathway, or combinations thereof. In some configurations, the norovirus-permissive cells can be transformed macrophages selected from the group consisting of RAW 264.7 cells, J774A.1 cells and WBC264-9C cells.

In various configurations, methods of detecting norovirus in a biological sample can also involve performing a cytopathic assay, an antibody assay, a nucleic acid detection assay, or a protein detection assay. A cytopathic assay can be, in some configurations, a dye exclusion assay, an enzyme release assay, a necrosis assay or an apoptosis assay. In some configurations, an antibody assay can use a monoclonal or a polyclonal antibody, such as an antibody directed against a norovirus polypeptide and any antigen detection system known in the art, such as a Western blot assay, an ELISA assay, an immunofluorescence assay, an immunoprecipitation assay or a radioimmunoassay. In yet other configurations, a nucleic acid detection assay can be an assay such as a polymerase chain reaction assay or a hybridization assay such as a Northern blot assay.

In various embodiments, the invention can comprise methods of identifying a compound having anti-viral activity. In certain configurations, a method can comprise contacting the compound with a norovirus-permissive cell culture infected with a norovirus, and detecting inhibition of norovirus replication. Detecting inhibition of viral replication in these embodiments can comprise detecting inhibition of viral nucleic acid synthesis or viral protein synthesis. In some configurations, detecting inhibition of norovirus replication can comprise performing a plaque assay on the norovirus-permissive cell culture. In these configurations, the assays for identifying anti-viral compounds can be used for identifying compounds having anti-RNA virus activity, anti-single-stranded RNA virus activity, anti-positive strand single-stranded RNA virus activity, anti-positive strand single-stranded RNA, no DNA stage virus activity, anti-calicivirus activity, or anti-norovirus activity. A norovirus infecting a norovirus-permissive cell in these methods can be, in certain configurations, a norovirus comprising a nucleic acid consisting of from about 7200 to about 7700 nucleotides and wherein the norovirus nucleic acid hybridizes under high stringency conditions to a nucleic acid consisting of the sequence set forth in SEQ ID NO: 1.

In various embodiments, the invention can comprise a host range-modified norovirus. In some configurations, a host range-modified norovirus can be a norovirus adapted for growth in fibroblasts or macrophage-lineage cells which are not anti-viral pathway-deficient. In certain aspects, a host range-modified Norovirus can exhibit reduced virulence compared to non-adapted norovirus infecting the same host cells. A host range-modified norovirus of these embodiments can be, in certain aspects, a norovirus comprising an RNA of at least about 7200 to about 7700 nucleotides, wherein the RNA consists of a nucleotide sequence at least 80% identical to the RNA of the norovirus deposited with ATCC on Apr. 27, 2004 as Accession Number PTA-5935. A host range-modified norovirus can have a reduced virulence against a host organism compared to a non-adapted norovirus. In certain configurations, a host range-modified norovirus can be used for vaccination against norovirus infection. Hence, a norovirus vaccine can comprise a therapeutically effective amount of a host range-modified norovirus.

In various embodiments, the invention comprises methods of adapting norovirus to have a modified host range. The methods can also comprise serially passaging a norovirus population for three or more generations in norovirus-permissive cell cultures. The serially passaging can comprise plaque-purifying a norovirus and growing the plaque-purified norovirus in norovirus-permissive host cells for three or more serial passages.

In some embodiments, the invention includes cDNA of norovirus genomic RNA. A cDNA in these embodiments can be single-stranded or double-stranded, and can be comprised by a vector, such as a plasmid or viral vector. In some configurations, a cDNA of a norovirus genomic RNA can comprise an infectious clone. In certain aspects, a cDNA of a norovirus genomic RNA can comprise a partial cDNA, such as, for example, a subgenomic replicon. A vector comprising a subgenomic replicon can further comprise a reporter sequence, for example a reporter sequence encoding an enzyme or a green fluorescent protein. Such constructs can be used to test the efficacy of a candidate anti-viral compound.

BRIEF DESCRIPTION OF THE DRAWINGS

FIG. 1 illustrates productive infection in vitro by brain homogenate-derived norovirus of STAT-deficient macrophages, RAW 264.7 cells and dendritic cells.

FIG. 2 illustrates virus grown from plaques from the culture system infected with MNV-1.

FIG. 3 illustrates growth of plaque-derived MNV-1.CW1 virus in bone marrow-derived macrophages, and RAW 264.7 cells.

FIG. 4 illustrates multi-step and single-step growth curves of plaque-derived MNV-1 in in anti-viral pathway-deficient macrophages.

FIG. 5 illustrates that a Type I interferon response and STAT-1 are required to prevent MNV-1 replication in bone marrow macrophages in vitro.

FIG. 6 illustrates MNV-1 infection in established macrophage cell lines including a human-mouse fusion cell line.

DETAILED DESCRIPTION

Methods and compositions for culturing norovirus are described herein. The methods and compositions described herein utilize laboratory techniques well known to skilled artisans and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999.

The present inventors have succeeded in discovering a cell culture system for a norovirus. Development of their methods involved the discovery of norovirus-permissive host cells. As used herein, a "norovirus-permissive cell" is a cell in which a norovirus replicates following infection with a norovirus or transfection with norovirus genome RNA. As used herein, "norovirus replication" can be understood to include various stages in norovirus life cycle, such as, for example, binding of a norovirus to a host cell, entry into the host cell, trafficking, processing, genome release, translation, transcription, assembly, and release. Norovirus replication can also be detected by measuring norovirus protein activity, for example polyprotein protease activity, viral RNA polymerase activity, VPG activity and NTPase activity. Thus, in some configurations, measurement of an increased accumulation of viral RNA or viral protein in infected cells can be considered an indication of viral replication, although an increase in virus particle production is not measured. Hence, in certain configurations, in a test of a candidate anti-viral agent, anti-viral activity can be detected by detecting inhibition of a norovirus protein activity, such as inhibition of polyprotein protease activity, viral RNA polymerase activity, VPG activity or NTPase activity. In other configurations, in a test of a candidate anti-viral agent, anti-viral activity can be detected by detecting inhibition of a norovirus protein accumulation, such as inhibition of polyprotein protease accumulation, viral RNA polymerase accumulation, VPG accumulation or NTPase accumulation.

The norovirus-permissive culture and the accompanying methods can be used for a variety of purposes, such as diagnostic methods, development of assays for viral replication, selection of mutant viruses with desirable properties, identification of mutant viruses, screening of potential anti-viral compounds, and development of vaccines.

As used herein, the term "norovirus" can refer to unmodified, wild-type norovirus, e.g., norovirus obtained from an individual with viral gastroenteritis, unless specified otherwise. As used herein, the term "host range-modified norovirus" refers to norovirus modified, with regard to its host range, using laboratory methods, e.g., norovirus grown in vitro for multiple passages.

In various embodiments, the present invention can comprise a norovirus-permissive cell culture infected with a norovirus. A norovirus permissive cell culture can be maintained using routine cell culturing techniques well known to skilled artisans. A norovirus-permissive cell culture can comprise vertebrate cells, such as macrophage-lineage cells and DC-lineage cells. As used herein, the term "macrophages" refers to mononuclear phagocytes found in blood and tissues, and the term "dendritic cells" refers to reticular, immunocompetent antigen presenting cells of the lymphoid and haemopoietic systems, blood and skin. Macrophage-lineage cells and DC-lineage cells can comprise haematopoietic-lineage cells that can be either mature in their differentiation state as macrophages or DCs, respectively, or partially mature, i.e., macrophage or DC-like cells which exhibit some of the known characteristics of macrophages and DCs. Macrophage-lineage cells and DC-lineage cells can also comprise precursor cells to mature macrophages or DCs, such as, for example, bone marrow cells, peripheral blood monocytes, or circulating DC-lineage precursor cells. Because treatment of macrophage-lineage cells or DC-lineage cells with cytokines, interleukins, chemokines, or other reagents (for example, CSF-1, GM-CSF, TNF-α, lipopolysaccharide (LPS) or CD40 Ligand) can influence the differentiation state of cells (e.g., Sapi E., Exp. Biol. Med. 229:1-11 2004; Dieu, M.-C. et al., J. Exp. Med. 188: 373-386, 1988) the differentiation state of many haematopoietic lineage cells can be altered by such treatments to become norovirus-permissive. Hence, in non-limiting example, macrophage-lineage cells or DC-lineage cells can be, respectively, macrophages or DCs such as bone marrow macrophages or DCs, umbilical cord macrophages or DCs, and peripheral blood mononuclear cells. Norovirus-permissive cells can therefore include, for example, cytokine-stimulated macrophage-lineage cells such as, for example, cytokine-stimulated macrophages such as bone marrow macrophages, cytokine-stimulated umbilical cord macrophages, cytokine-stimulated peripheral blood mononuclear cells, and cytokine-stimulated peripheral blood macrophages, or cytokine-stimulated DCs such as, for example, cytokine-stimulated DCs such as bone marrow DCs, cytokine-stimulated umbilical cord DCs, and cytokine-stimulated peripheral blood DCs. For example, mature, wild type macrophages harvested from peripheral blood but otherwise untreated may not be norovirus-permissive. However, treatment of such cells with an appropriate stimulus, such as, for example, a cytokine such as CSF-1, may alter the macrophages to become norovirus-permissive. In certain configurations, norovirus-permissive cells can be macrophages or DCs derived from embryonic stem cells. The embryonic stem cells can be stimulated to become macrophages or DCs using methods well known in the art (e.g., Senju, S. et al., Blood 101: 3501-3508, 2003).

In certain embodiments, macrophages and DCs support norovirus replication. The macrophages which can support norovirus replication can be macrophages deficient in one or more anti-viral pathways. The deficiency in a cellular anti-viral pathway can be a deficiency in a STAT-1-dependent anti-viral pathway, a deficiency in an interferon receptor-dependent anti-viral pathway, a deficiency in a double-stranded RNA-dependent serine/threonine protein kinase (PKR) anti-viral pathway (Hovanessian, A. G. Semin. Virol. 4, 237-245, 1993), or combinations thereof. Accordingly, macrophages which can support norovirus replication can be, in some configurations, STAT-1-deficient macrophages, PKR-deficient macrophages, or interferon receptor-deficient macrophages. The interferon receptor deficient macrophages can be deficient in a Type I interferon response. In some configurations, a norovirus-permissive macrophage can be deficient for an interferon-αβ receptor, deficient for an interferon-γ receptor, deficient for an interferon λ receptor, or a combination thereof. Macrophages deficient in the PKR-dependent anti-viral pathway can be macrophages deficient in PKR.

In certain configurations, the macrophage lineage cells can be transformed macrophages. In some aspects, transformed macrophages can be established macrophage cell lines such as, for example, RAW 264.7 cells, J774A.1 cells or WBC264-9C cells, all of which are available from the American Type Culture Collection, P.O. Box 1549, Manassas Va. 20108.

In certain configurations, the DC lineage cells can be bone marrow DCs, peripheral blood DCs, or transformed DCs. The DCs can be from any stage or substage of DC development or differentiation (e.g., Herbst, B., et al., Br. J. Haematol. 99: 490-499, 1997).

In some embodiments, the vertebrate cells can be murine cells, while in other embodiments, the vertebrate cells can be human cells. Human cells can be, for example, human bone marrow macrophages or dendritic cells. In some configurations, a norovirus can be a murine norovirus, while in other configurations, a norovirus can be a human norovirus, such as a Norwalk virus.

In various embodiments, the present invention can involve methods of replicating a norovirus in vitro. The methods can comprise inoculating norovirus-permissive cells with a norovirus, and culturing the cells. In these embodiments, inoculating norovirus-permissive cells can comprise infecting the cells with the norovirus, or transfecting the norovirus-permissive cells with a nucleic acid comprising a norovirus genome or a portion thereof comprising at least 25 contiguous nucleotides. In some embodiments, inoculating norovirus-permissive cells with a norovirus can comprise inoculating the cells with DNA such as a cDNA of a norovirus genome or a portion thereof comprising at least 25 contiguous nucleotides. The cDNA of a norovirus can be comprised by a vector, such as, in non-limiting example, a bacteriophage or a plasmid. In certain aspects, the cDNA can comprise a replicon, or a sequence encoding a viral polypeptide. A vector can further comprise a promoter, which can be operably linked to a sequence encoding a reporter polypeptide. In certain embodiments, a cDNA of a norovirus genome can be comprised by an infectious clone. In various configurations, the methods can comprise inoculating vertebrate cells which can be macrophage-lineage cells or DC-lineage cells. The macrophage-lineage cells which can be inoculated can be macrophage-lineage cells deficient in a cellular anti-viral pathway such as a STAT-1-dependent anti-viral pathway, an interferon receptor-dependent anti-viral pathway, a PKR-dependent anti-viral pathway, or a combination thereof. The macrophages deficient in an interferon pathway which can be inoculated can be deficient in an interferon-$\alpha\beta$ receptor, an interferon-$\gamma$ receptor, an interferon-$\lambda$ receptor or a combination thereof. The macrophages deficient in the PKR-dependent pathway which can be inoculated can be PKR-deficient macrophages. In some configurations, the macrophage-lineage cells which can be inoculated can be transformed macrophages such as RAW 264.7 cells, J774A.1 cells or WBC264-9C cells. Other macrophage-lineage cells, for example macrophage-lineage cells available from the American Type Culture Collection, can also be used to practice the methods of the invention. In certain configurations, the norovirus-permissive cells which can be inoculated with norovirus can be DCs such as bone marrow DCs, peripheral blood DCs, and transformed DCs.

In various embodiments of the invention, cells that can be inoculated with norovirus can be vertebrate cells such as human or murine cells, and the norovirus can be a murine norovirus or a human norovirus such as a Norwalk virus.

In various embodiments, the invention comprises methods of detecting norovirus in a biological sample. The methods can comprise contacting a cell culture comprising norovirus-permissive cells with the sample, and detecting norovirus viral replication in the cell culture. The sample in some configurations can be a diagnostic sample, such as a diagnostic sample from a mammal suspected of infection with the norovirus. The mammal can be a human, a laboratory animal such as a rodent, for example a mouse, a rat, or a guinea pig, a farm animal such as a cow or a sheep, or a companion animal such as a cat or dog. The diagnostic sample can be a tissue sample, a blood sample, or a stool sample. A tissue sample can be from any tissue or body fluid that is suspected of infection with a norovirus, such as, for example, liver, kidney, brain, blood, or saliva. The norovirus-permissive cells in these embodiments can be DC-lineage cells or macrophage-lineage cells. The macrophage-lineage cells can be macrophages deficient in a cellular anti-viral pathway such a STAT-1-dependent anti-viral pathway, an interferon receptor-dependent anti-viral pathway, a PKR-dependent anti-viral pathway, or combinations thereof. In some configurations, the macrophage-lineage cells can be transformed macrophages. The transformed macrophages can be, for example, transformed macrophages selected from the group consisting of RAW 264.7 cells, J774A.1 cells and WBC264-9C cells.

In various configurations, a method of detecting norovirus in a biological sample can comprise detecting a host cell change that results from norovirus infection. A host cell change can be, for example, a change in morphology, molecular composition, or cytopathicity. Hence, a method for detecting norovirus in a biological sample can comprise performing a cytopathic assay, an antibody assay, a protein detection assay or a nucleic acid detection assay. A cytopathic assay can be, in some configurations, a dye exclusion assay, an enzyme release assay, a necrosis assay, or an apoptosis assay. A dye exclusion assay can be, in non-limiting example, a trypan blue exclusion assay, or a fluorescent dye exclusion assay such as a propidium iodide exclusion assay. In some configurations, an antibody assay can use a monoclonal or a polyclonal antibody, such as a monoclonal antibody directed against a norovirus polypeptide, such as, for example, monoclonal antibody A6.2. Any antigen detection system known in the art, such as a Western blot assay, an ELISA assay, an immunofluorescence assay, an immunoprecipitation assay or a radioimmunoassay, can be used to detect the presence and/or quantity of a norovirus. In some configurations, a protein detection assay can comprise, in non-limiting example, a gel electrophoresis assay, a column chromatography assay, and an enzyme assay. In yet other configurations, a nucleic acid detection assay can be an assay such as a polymerase chain reaction assay or a hybridization assay such as a Northern blot assay.

In various embodiments, the invention comprises methods of identifying a compound having anti-viral activity. "Anti-viral activity," as used herein, can comprise inhibiting viral activity at any stage in a virus' life cycle. Hence, anti-viral activity can comprise, in non-limiting example, inhibition of viral replication, inhibition of viral gene expression, or inhibition of a viral protein accumulation or activity. Inhibition of a viral protein accumulation or activity can comprise, in non-limiting example, inhibition of norovirus polyprotein protease accumulation, inhibition of norovirus RNA polymerase accumulation, inhibition of norovirus VPG accumulation, inhibition of norovirus NTPase accumulation, inhibition of norovirus polyprotein protease activity, inhibition of norovirus RNA polymerase activity, inhibition of norovirus VPG activity, or inhibition of norovirus NTPase activity. Standard methods well known in art the for measuring or detecting norovirus protein accumulation or activity can be used, for example, enzyme assays and antibody assays.

In certain configurations, a method for identifying a compound having anti-viral activity can comprise contacting a candidate anti-viral compound with a norovirus-permissive cell culture infected with a norovirus, and detecting inhibition of norovirus replication. In certain aspects, a candidate anti-viral compound can be added to an infected norovirus-permissive culture at a concentration of from about 1 picomolar to about 100 millimolar, or from about 1 nanomolar to about 100 micromolar. Detecting inhibition of viral replication in some embodiments can thus comprise detecting inhibition of viral nucleic acid synthesis or viral protein synthesis. In some configurations, detecting inhibition of norovirus replication can comprise performing a plaque assay on the norovirus-permissive cell culture. A plaque assay can comprise determining a titer of virus accumulated in a plaque formed by infected cells in the presence of the candidate anti-viral molecule. In these configurations, assays for identifying anti-viral compounds can be used for identifying compounds having anti-RNA virus activity, anti-single-stranded RNA virus activity, anti-positive strand single-stranded RNA virus activity, anti-positive strand single-stranded RNA, no DNA stage virus activity, anti-calicivirus activity, or anti-norovirus activity. A norovirus infecting a norovirus-permissive cell in these methods can be, in certain configurations, a norovirus comprising a nucleic acid consisting of from about 7200 to about 7700 nucleotides and wherein the norovirus nucleic acid hybridizes under high stringency conditions to a nucleic acid consisting of the sequence set forth in SEQ ID NO: 1. In some configurations, anti-viral activity can be detected by detecting differences between infected norovirus-permissive cells contacted with a candidate anti-viral agent and control infected norovirus-permissive cells. Such differences can comprise, in non-limiting example, gene expression differences, antigenic differences, enzyme activity differences, dye-staining differences, or morphological differences (as revealed by light microscopy or electron microscopy). In some configurations, anti-viral activity can be detected by performing a cytopathic effects (CPE) inhibition assay in which the anti-viral activity reduces or prevents norovirus-induced CPE.

In various embodiments, the invention comprises a host range-modified norovirus. In some configurations, a host range-modified norovirus can be a norovirus adapted for growth in fibroblasts or macrophage-lineage cells which are not anti-viral pathway-deficient. In certain aspects, a host range-modified norovirus can exhibit reduced virulence compared to non-adapted norovirus infecting the same host cells. A host range-modified norovirus of these embodiments can be, in certain aspects, a norovirus comprising an RNA of at least about 7200 to about 7700 nucleotides, wherein the RNA consists of a nucleotide sequence at least 80% identical to the RNA of the norovirus deposited on Apr. 27, 2004 with ATCC as Accession Number PTA-5935.

A host range-modified norovirus can have reduced virulence against a host cell or organism compared to a non-adapted norovirus. In certain configurations, a norovirus vaccine can comprise a therapeutically effective amount of a host range-modified norovirus. A therapeutically effective amount of a host range-modified norovirus for use as a vaccine can comprise, for example, from 1 to about 1,000,000 plaque forming units of a host range-modified norovirus. In certain configurations, a host range-modified norovirus can be a norovirus adapted to grow in a host cell that is approved by a government regulatory agency such as the US Food and Drug Administration for the production of a vaccine. An approved host cell can be, for example, Vero cells such as cells having an ATCC designation of No. CCL-81.

In various embodiments, the invention comprises methods of adapting norovirus to have a modified host range. The methods can comprise serially passaging a norovirus population for three or more generations in norovirus-permissive cell cultures. The serially passaging can comprise plaque-purifying a norovirus and growing the plaque-purified norovirus in norovirus-permissive host cells for two serial passages, three serial passages, or more serial passages. Hence, examples of host cells for a norovirus adapted to a modified host cell range can include not only RAW 264.7 cells, J774A.1 cells, WBC264-9C cells, anti-viral pathway-deficient macrophages and dendritic cells, but also fibroblasts such as embryonic fibroblasts, and wild type macrophages (i.e., macrophages that are not deficient in a cellular anti-viral pathway). In some configurations, adapting the host range-modified norovirus to growth in a vaccine production-approved cell line can comprise infecting the approved cell line with host range-modified norovirus, and growing the virus. Methods for producing a vaccine against a virus using a virus exhibiting reduced virulence through serial passage adaptation (Sabin, A. B., Ann. N Y Acad. Sci. 61: 924-938, 1955) or through genetic engineering (e.g., by altering codons) are well known to skilled artisans.

The invention can be further understood by reference to the examples which follow.

EXAMPLE 1

This example illustrates methods for growth and harvesting of cells and cell lines used for investigating norovirus growth in vitro.

In this example, murine embryo fibroblasts were obtained and cultured as described in Pollock et al., Virology 227: 168-179, 1997, or according to instructions provided by the supplier. RAW 264.7 cells were purchased from the American Type Culture Collection and maintained in Dulbecco's Modified Eagle's Medium (DMEM) supplemented with 10% low-endotoxin fetal calf serum (FCS, HyClone, Logan, Utah, cat # SH30070.03), 100 U penicillin/ml, 100 µg/ml streptomycin, 10 mM N-2-hydroxyethylpiperazine-N'-2-ethanesulfonic acid (HEPES), and 2 mM L-glutamine (Biosource, Camarillo, Calif.). Macrophages were harvested from bone marrow and cultured as described in Heise et al., Virology 241: 331-344, 1998. Dendritic cells were obtained by suspending bone marrow cells in RPMI 1640 medium containing 10% low endotoxin FCS, 2 mM L-glutamine, 1 mM sodium pyruvate (Biosource), 100U penicillin/ml, 100 µg/ml streptomycin, 1% non-essential amino acids (Biosource) and 20 ng/ml recombinant mouse GM-CSF (BD Biosciences, San Jose, Calif.), and plating the cells at a concentration of $3 \times 10^5$ cells/ml in 6 well plates (3 ml/well). The percentage of $CD11c^+$ DCs was determined by FACS analysis after culturing cells for seven days at 37° C. and 5% $CO_2$. Around 70% of the cells were CD11c-positive. 129 wild-type and STAT1−/− mice were purchased from Taconic (Germantown, N.Y.). Interferon (IFN) αβ receptor (R)−/− mice, IFNγR−/− mice, and IFN αβγR−/− mice (Muller et al., Science 264, 1918-1921, 1994), protein kinase R −/− mice (Yang et al., EMBO J. 14, 6095-6106, 1995), and inducible nitric oxide (iNOS)−/− mice (MacMicking et al., Cell 81, 641-650, 1995) were bred and housed at Washington University in accordance with all federal and university policies.

EXAMPLE 2

This example illustrates methods for infection of cells with norovirus.

In this example, as shown in FIG. 1A, adherent cells were plated in 12 well plates at $2 \times 10^5$ or $5 \times 10^5$ cells per well and allowed to attach for several hours. Infections were carried out at an M.O.I. of 0.05 (for multi-step growth curves, FIG. 1) or M.O.I. of 2.0 (for single-step growth curves and other timecourse experiments, FIG. 3) for 30 min on ice in a volume of 0.5 ml per well. DCs were infected in bulk. Cells were then washed extensively with 2×2 ml of ice-cold PBS per well. To allow viral entry, 1 ml of media was added to each well and cells were incubated at 37° C. and 5% $CO_2$ for different time periods. Growth curve samples were subjected to two or three cycles of freeze/thawing before titering. These data show that MNV-1 replicates in macrophages, DC's, and RAW cells.

In this example and throughout the application, the following abbreviations and acronyms apply:

| Abbreviation | Definition |
| --- | --- |
| 10H2 | Monoclonal antibody 10H2 |
| A6.2 | Monoclonal antibody A6.2 |
| B1-3 | Brain homogenate B1-3 |
| DC | Dendritic Cell(s) |
| h.p.i. | Hours post infection |

-continued

| Abbreviation | Definition |
|---|---|
| IFN | Interferon |
| IFN-αβR-/- | Interferon-αβ receptor-deficient |
| IFN-γR-/- | Interferon-γ receptor-deficient |
| iNOS-/- | Inducible nitric oxide-deficient |
| J774 | J774 cells |
| M.O.I. | Multiplicity of Infection |
| mAB | Monoclonal antibody |
| Mac | Macrophage(s) |
| MEF | Murine Embryonic Fibroblast(s) |
| MNV | Murine norovirus, murine norovirus-1, or strain CW1 of murine norovirus-1 |
| MNV-1 | Murine norovirus-1 or Strain CW1 of murine norovirus-1 |
| MNV-1.CW1 | Strain CW1 of murine norovirus-1 |
| Mφ | Macrophage(s) |
| P1, P3 | Passage 1 or Passage 3, respectively |
| Pfu | Plaque forming units |
| PKR-/- | Double-stranded RNA-dependent serine/threonine protein kinase-dependent anti-viral pathway-deficient |
| RAW | RAW 264.7 cells |
| STAT1-/- | STAT-1 deficient cells |
| VP1 | Viral protein 1; MNV-1 capsid protein |
| WBC | WBC264-9C cells |
| WT | Wild type |

EXAMPLE 3

This example illustrates a mouse norovirus-1 plaque assay.

In this example, as illustrated in FIG. 1A and FIG. 1B, RAW 264.7 cells were seeded into 6 well plates at a density of $2 \times 10^6$ viable cells. On the following day, 10-fold dilutions of virus inoculum were prepared in complete DMEM and plated in duplicate wells. Plates were incubated for one hour at room temperature on a rocking apparatus before aspirating the inoculum and overlaying the cells with 2 ml of 37-40° C. 1.5% SeaPlaque® agarose (CBM Intellectual Properties, Inc.) in MEM supplemented with 10% low-endotoxin FCS, 1% HEPES, 1% penicillin/streptomycin, and 2% glutamine (complete MEM). Plates were incubated at 37° C. and 5% $CO_2$ for 2 days. To visualize plaques, cells were stained with 2 ml of 56° C. 1.5% SeaKem® agarose (FMC Corporation) in complete MEM containing 1% Neutral Red for 6-8 hours. These data show that MNV-1 replication can be quantified using a plaque assay.

EXAMPLE 4

This example illustrates a mouse norovirus-1 plaque neutralization assay method.

In this example, as shown in FIGS. 2E and 2F, differing concentrations of purified monoclonal antibody (A6.2=anti-MNV-1 capsid, isotype control=10H2, anti-μ1c reovirus) were incubated with 2000 pfu of either MNV-1.CW1 or MNV-1 brain homogenate for 30 min at 37° C. prior to performing the MNV-1 plaque assay as described in Example 3. These data show that the plaques are due to MNV-1 and that an antibody can block infection with MNV-1.

EXAMPLE 5

This example illustrates methods for Cesium Chloride purification of mouse norovirus-1.

In this example, as shown in FIGS. 2A, 2B, 2C and 2D, RAW cells were infected with MNV-1.CW1 for 2 days with an MOI=0.05. Cellular debris was removed from the freeze/thaw lysate by low speed centrifugation. The supernatants were layered on top of a 5 ml 30% sucrose cushion and centrifuged at 4° C. for 2.5 hours at 27,000 rpm (90,000×g) in a SW32 rotor. The cell pellets were then resuspended in PBS and mixed with CsCl to a final density of 1.33 g/cm³ and centrifuged for at least 18 hours at 35,000 rpm (115,000×g) in a SW55 rotor. A wide lower and narrow upper band were typically seen in the gradient. The lower band was collected by puncturing the side of the tube with a needle before overnight dialysis against PBS at 4° C. These data show that the virus growing is MNV-1 and is a norovirus.

EXAMPLE 6

This example illustrates methods for protein analysis using SDS-polyacrylamide gel electrophoresis and Coomassie blue staining.

In this example, as illustrated in FIG. 2B, CsCl-purified virions were separated by SDS-PAGE using standard procedures (Laemmli, U.K., Nature, 227: 680-685, 1970). Proteins were visualized by Coomassie staining using the Simply Blue™ safe stain (Invitrogen, Carlsbad, Calif.) according to manufacturer's instructions. These data, together with data shown in FIG. 2C, show that the virus growing in the cells contains the MNV-1 capsid protein.

EXAMPLE 7

This example demonstrates Western blot analysis methods.

In this example, as shown in FIG. 2C, proteins were transferred to a nitrocellulose membrane and incubated with a rabbit polyclonal antibody directed against MNV-1 capsid protein, followed by a peroxidase-labeled secondary antibody. Antibody binding was visualized using ECL™ chemiluminescence (Amersham Biosciences, Piscataway, N.J.) according to the manufacturer's instructions. The data show that the capsid in the growing virus is the MNV-1 capsid protein.

EXAMPLE 8

This example illustrates Northern blot analysis methods.

In this example, as shown in FIG. 2D, probes for Northern blot analysis were generated by linearizing and gel purifying plasmid DNA containing portions of the MNV-1 genome (nt 5617-7039) digested with restriction endonuclease NcoI (for a positive-sense probe) or restriction endonuclease SpeI (for a negative-sense probe). Labeled probes were generated by performing a standard $p^{32}$ radioactive transcription assay using SP6 or T7 RNA polymerase (Roche, Germany) according to manufacturer's recommendations. Total RNA from virus-infected or mock-infected cells were isolated using Trizol (Invitrogen, Carlsbad, Calif.) according to manufacturer's recommendations. Northern blotting was performed using standard protocols. Probes were hybridized overnight at 68° C. The data show that the RNA in the growing virus is MNV-1 RNA.

EXAMPLE 9

This example illustrates ELISA analysis methods.

In this example, as illustrated in FIG. 2E, ELISA was performed as described in Karst, S. M. et al., Science 299: 1575-1578, 2003, with the following modifications. ELISA plates were coated overnight at 4° C. with CsCl-purified MNV-1 particles at 0.2 or 1.0 mg/well. Diluted, purified anti-MNV-1 capsid monoclonal antibody A6.2 and anti-reovirus isotype control monoclonal antibody 10H2 were applied to coated wells, followed by a peroxidase-labeled secondary antibody. Antibodies were incubated in wells for 60 min. at 37° C. These data show that the A6.2 monoclonal antibody binds specifically to MNV-1.

EXAMPLE 10

This example illustrates electron microscopy methods used to image mouse MNV-1.

In this example, as shown in FIG. 2A, samples of CsCl-purified MNV-1 virions were negatively stained and observed using an electron microscope, as described in Karst et al., supra. The morphology of the observed particles is consistent with that of a virus. The data show that the growing virus is a norovirus.

EXAMPLE 11

This example illustrates lytic growth of a norovirus, MNV-1 (Karst, S. M. et al., Science 299: 1575-1578, 2003; U.S. Patent Application 60/440,016 of Virgin, "Murine Calicivirus" filed Jan. 14, 2003), in murine macrophage-lineage cells.

Figure 2:
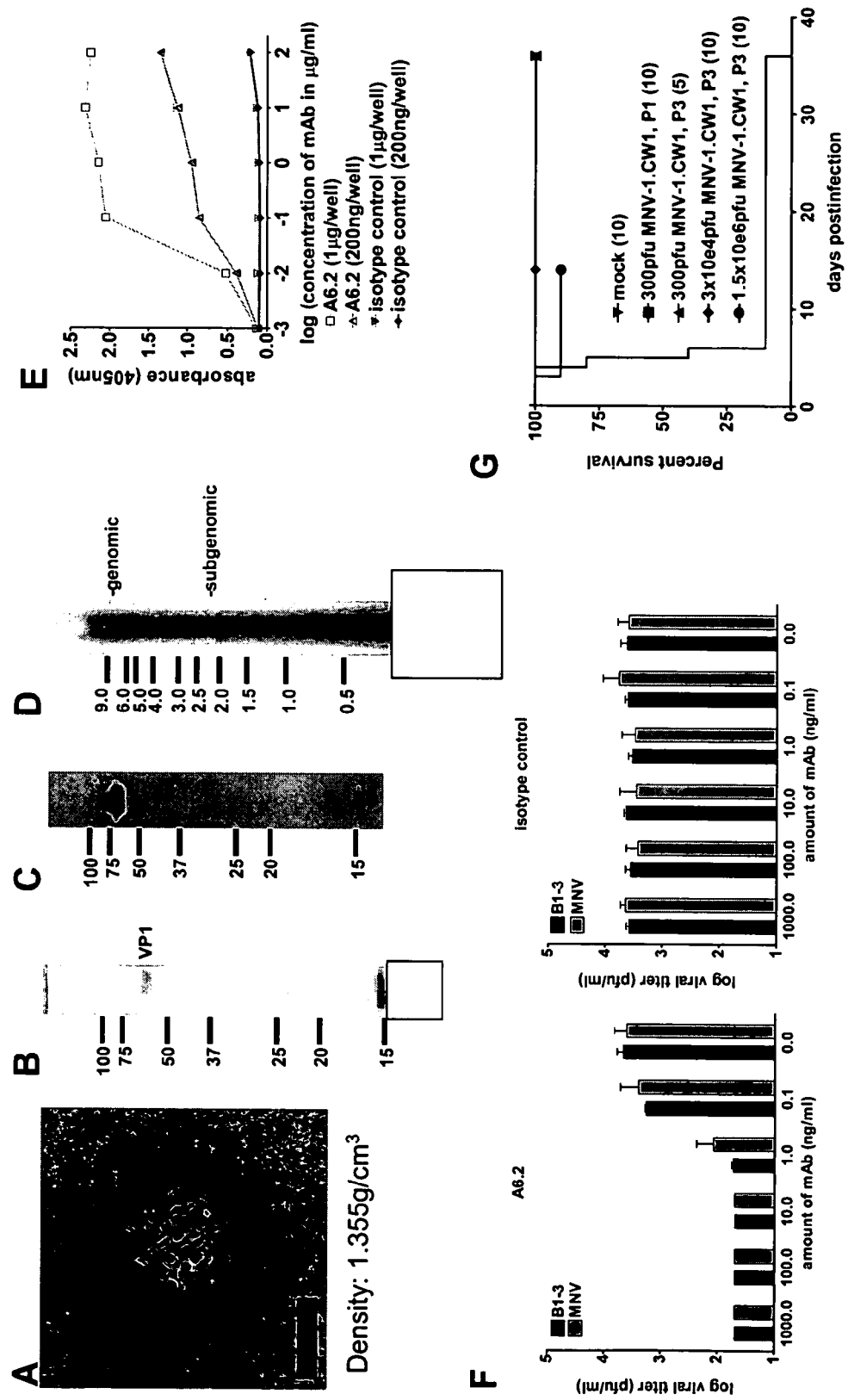
Figure 3:
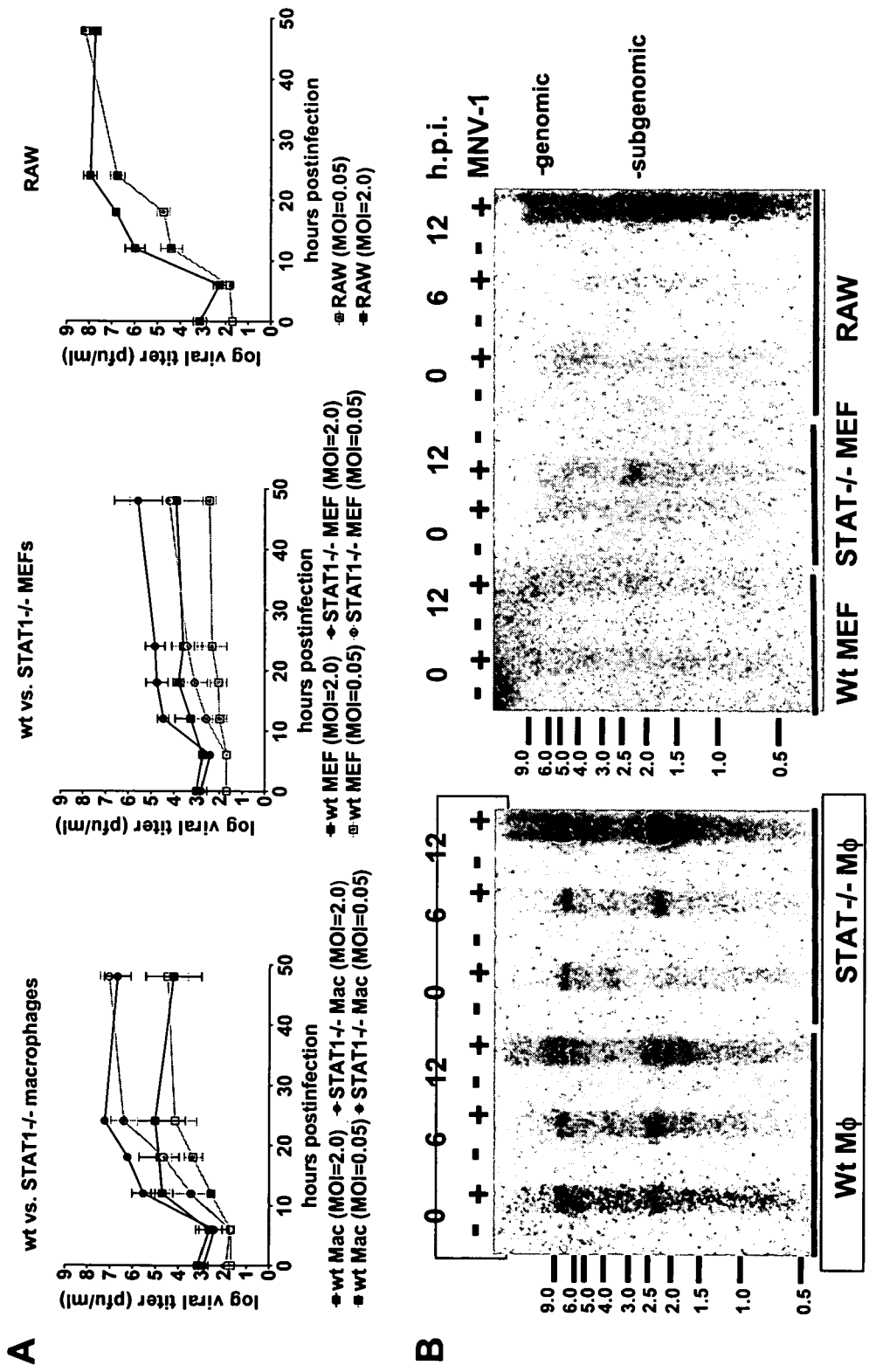

In this example, as shown in FIG. 3, macrophage-lineage cells, including primary murine STAT1-/- bone marrow derived macrophages and the murine macrophage cell lines RAW 264.7 and J774A.1, were infected with mouse norovirus MNV-1. As shown in FIG. 3A, each of these macrophage-lineage cell types supported viral replication and lytic growth. Using RAW 264.7 cells, a MNV-1 plaque assay was developed and used to study the viral life cycle (FIGS. 1A, 1B). While a cytopathic effect was visible in productively infected cells 24 hours postinfection (h.p.i.), virions were detected between 9 and 12 h.p.i. Virion production was preceded by the production of genomic and subgenomic RNAs as detected by Northern blot analysis (FIG. 3B). Growth in RAW cells for a single passage did not dramatically alter the virulence of MNV-1, as a plaque purified strain (MNV-1.CW) still caused lethal disease in STAT-/- mice after peroral inoculation (FIG. 2G MNV-1.CW1 passage 1). However, growth in RAW cells for three passages generated a virus stock with significantly decreased virulence towards STAT-/- mice (FIG. 2G, MNV-1.CW1 passage 3). This example demonstrates that MNV-1 can be cultured in macrophage-lineage cells, that macrophage-lineage cells can be norovirus-permissive cells, and that MNV-1 can lose its virulence upon serial passage in norovirus-permissive cells. Furthermore, this example shows that replication of viral RNA can be detected by Northern Blot analysis.

EXAMPLE 12

This example illustrates that MNV-1 productively infects STAT-deficient macrophages, RAW 264.7 cells and dendritic cells, and causes cytopathic effects in these cells.

In this example, as shown in FIG. 1, wild-type murine embryonic fibroblasts, STAT -/- embryonic fibroblasts, wild-type primary mouse macrophages, STAT-/- macrophages, wild-type DCs, STAT-/- DCs, and RAW 264.7 cells were examined for their permissiveness towards norovirus infection. In these experiments, the cells were initially obtained and grown under conditions described in Example 1, and contacted for 30 minutes on ice with an MNV-1-containing brain homogenate at a multiplicity of infection (M.O.I.) of 0.05. (A) Cells were subjected to freezing and thawing at various time intervals following contact with the MNV-1 brain homogenate. Virus production was the measured by titering using the plaque assay as described in Example 3. Each time point was repeated 2-3 times to generate standard errors of the mean. The data indicate that STAT -/- macrophages support significantly more virus production than wild type macrophages, while wild type DCs, STAT-/- DC's, and RAW cells all support significant amounts of virus production. (B) MNV-1 causes cytopathic effect in permissive cells. Cells contacted with MNV-1-containing brain homogenate as above, or mock infected with an uninfected brain homogenate, were cultured for two days and observed by light microscopy. Cytopathic effects of MNV-1 infection are evident in STAT-1-/- macrophage cultures, DC cultures (both wild type and STAT-/-), and RAW cell cultures, but not in mouse embryonic fibroblast cultures (either wild type or STAT-/-) nor wild type macrophage cultures.

EXAMPLE 13

This example illustrates that virus grown from plaques from norovirus-permissive cell cultures infected with MNV-1 is MNV-1.

In these experiments, MNV-1 was plaque purified three times in RAW 264.7 cells. The resulting virus strain was designated MNV-1.CW1. The MNV-1.CW1 was purified by CsCl buoyant density gradient centrifugation, then analyzed as shown in FIG. 2: (A) MNV-1.CW1 visualized by negative staining electron microscopy. CsCl gradient-purified MNV-1.CW1 particles show typical norovirus morphology. (B) SDS-polyacrylamide gel electrophoresis analysis of CsCl gradient-purified MNV-1.CW1 particles. A gel stained with Coomassie Brilliant Blue reveals that the virus particles comprise a large amount of a protein with the appropriate molecular weight for the MNV-1 capsid. (C) Western Blot analysis of CsCl gradient-purified MNV-1.CW1 particles. A polyacrylamide gel prepared similar to that shown in (B) was transferred to a membrane and probed with an antibody directed against recombinant MNV-1 capsid protein. The single prominent band corresponding to the protein band labeled "VP1" in (A) bound the antibody probe. Because of its reactivity with the antibody, the polypeptide comprising the band was deemed to be MNV-1 capsid protein. (D) Northern Blot analysis of RNA obtained from infected RAW 264.7 cells. Following separation according to size by gel electrophoresis, the RNA was transferred to a membrane and probed under high stringency conditions (Sambrook et al., supra) using a probe specific for the MNV-1 genome. The hybridization was much stronger for RNA from infected cells compared to uninfected control cells (data not shown). (E) ELISA analysis of CsCl gradient-purified MNV-1.CW1 particles. Virus particles were distributed to wells in an ELISA plate, and probed with monoclonal antibodies directed against either MNV-1 capsid protein (MAb A6.2) or a reovirus protein (MAb 10H2). Binding of the primary antibodies to the virus samples was detected using an enzyme-conjugated secondary antibody. The data indicate that MAb A6.2 specifically bound to the norovirus. (F) Plaque neutralization assay. Samples of MNV-1 brain homogenate or MNV-1.CW1 were incubated with increasing concentrations of MAb A6.2 or MAb 10H2 before performing a plaque assay. The data indicate that MAb A6.2 neutralizes the virus, while control, isotype-matched MAb 10H2 did not. Thus, a monoclonal antibody can be used as an anti-viral agent for inhibiting viral infection.

EXAMPLE 14

This example illustrates that bone marrow-derived macrophages and RAW 264.7 cells, are permissive for growth of MNV-1.CW1 virus, and that passaging of the norovirus increases its host cell range.

In these experiments, MNV-1.CW1 virus, as described above, was expanded three times in RAW 264.7 cells, yielding MNV-1.CW1 P3 virus, as shown in FIG. 3. Multi-step (M.O.I. 0.05) and single-step (M.O.I. 2.0) growth curves were generated using MNV-1.CW1 P3 virus on indicated cells. While the thrice-passaged virus stock retained the capacity to grow to high titers in the RAW 264.7 cells, it showed an increase in host range, in that it replicated in STAT-1-/-embryonic fibroblasts. Nonetheless, some selective permissiveness of the virus for viral growth in macrophages over fibroblasts was still retained, as shown by the higher titers obtained in macrophages versus murine embryonic fibroblasts. FIG. 3B shows Northern blot analysis of timecourse of viral RNA infection from cells infected with MNV-1.CW1 at an M.O.I. of 2.0, or mock-infected. h.p.i.=hours post infection. Analysis of the levels of viral RNA over time reveal that viral RNA synthesis was greater in macrophages than fibroblasts and greater in STAT-1-/- macrophages than in wild type macrophages. Together, these data indicate that noroviruses can adapt to grow in normally non-permissive cells in culture, while retaining sensitivity to STAT1-dependent antiviral effects.

EXAMPLE 15

This example illustrates mechanisms of MNV-1 growth control.

Figure 4:
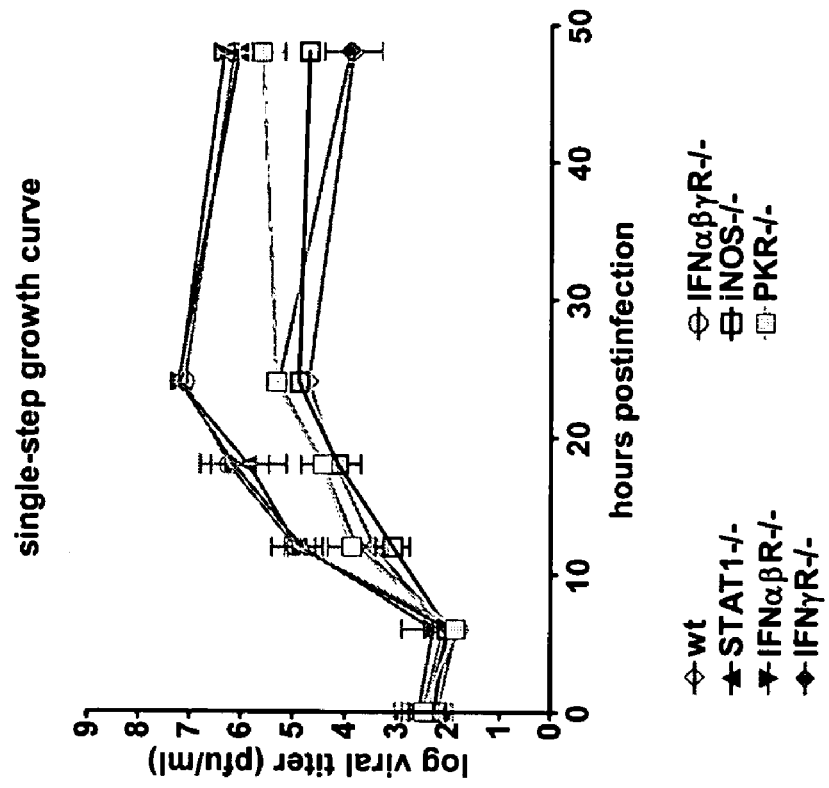
Figure 4:
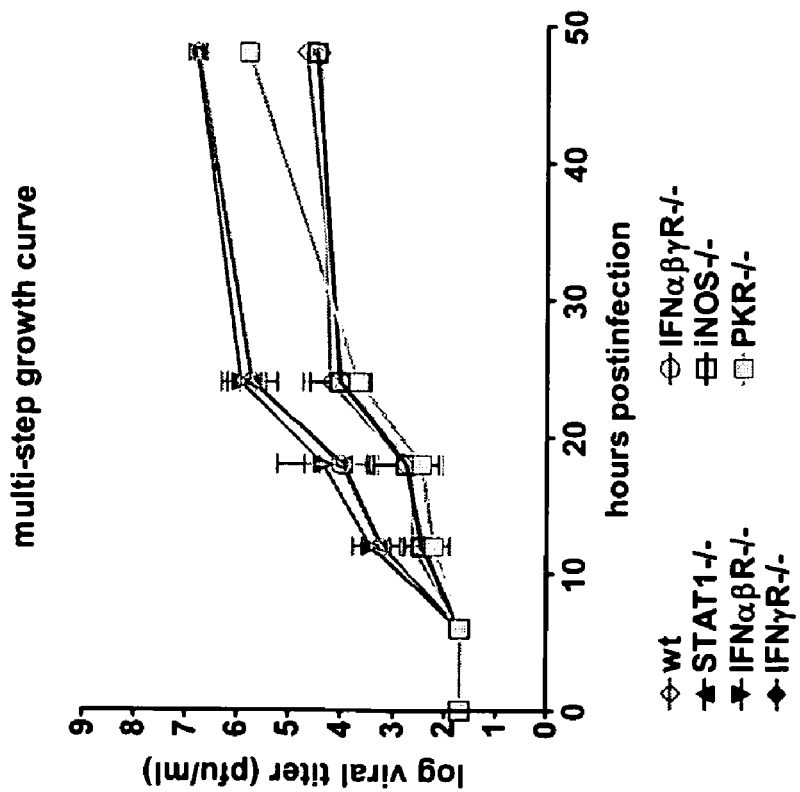

In these experiments, macrophages lacking specific components of the antiviral machinery were tested for their MNV-1 permissiveness. As shown in FIG. 4, MNV-1 growth in macrophages is controlled by STAT-1, type I interferon receptors and PKR. Multi-step (M.O.I.=0.05, left panel) and single-step (M.O.I.=2.0, right panel) growth curves of MNV1.CW1 in bone marrow-derived murine macrophages are shown. Macrophages from mice lacking the interferon-αβ receptor, STAT-1, or PKR all showed increased permissiveness for MNV-1 growth, demonstrating that these three molecules are part of the cellular response that limits norovirus growth. In contrast, deletion of other antiviral molecules, including iNOS and RNAseL, had no effect on MNV-1 growth.

EXAMPLE 16

This example illustrates that a Type I interferon response and STAT-1 are required to prevent MNV-1 replication in bone marrow macrophages in vitro, as measured by viral RNA production.

Figure 5:
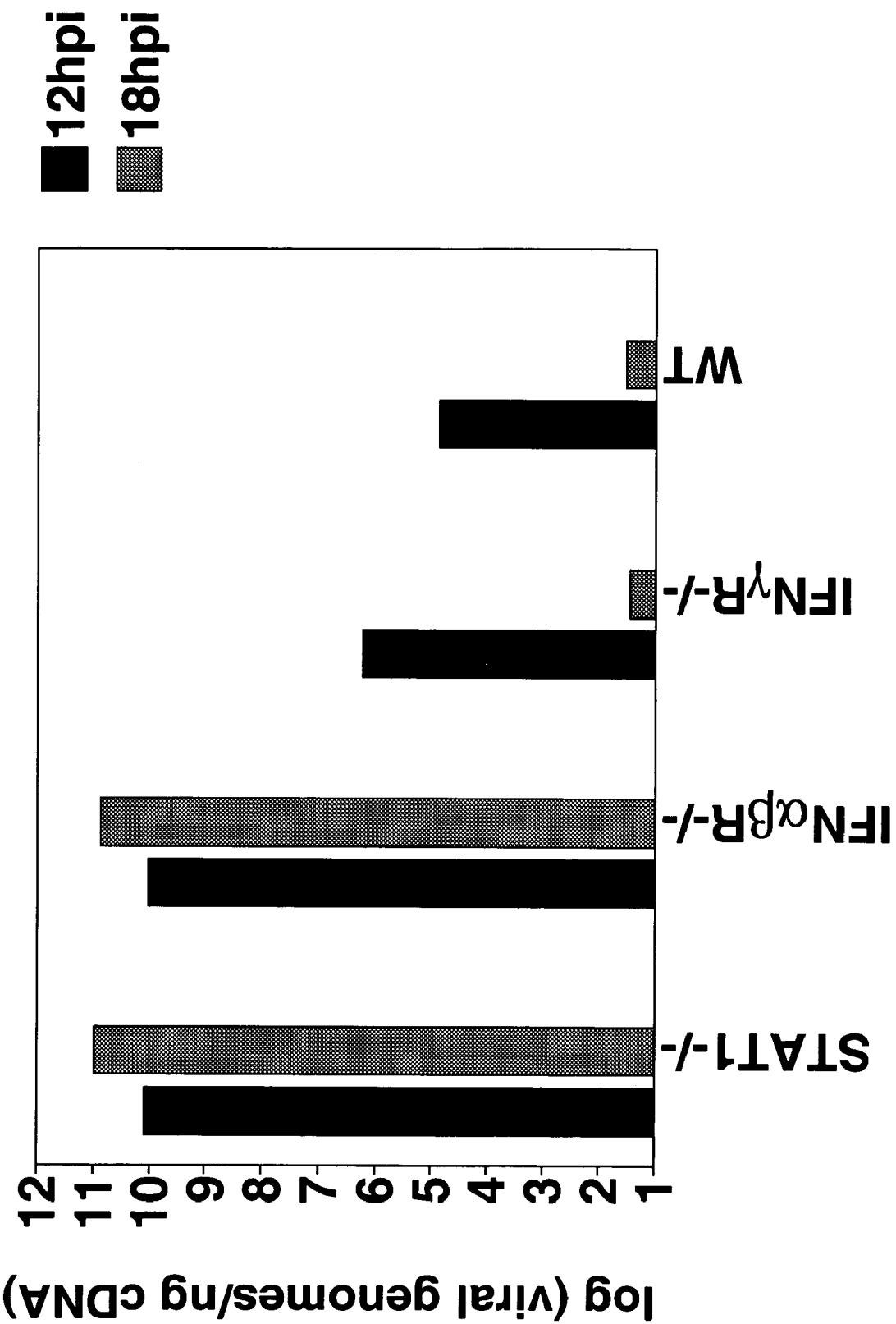

In these experiments, as shown in FIG. 5, accumulation of viral genomes in infected macrophages was measured using quantitative real time PCR (Karst, S. M. et al., Science 299: 1575-1578, 2003). STAT-1-deficient (STAT-1-/-), interferon-αβ receptor-deficient (IFN-αβR-/-), interferon-γ receptor-deficient (IFN-γR-/-), or wild type bone marrow macrophages were infected with MNV-1, as discussed supra. At 12 hr and 18 hr post infection (h.p.i.), cells were lysed and cDNA prepared from cellular RNA. The number of viral genomes as normalized to cDNA levels was then determined. The results show that viral RNA expression can be measured to assess replication, and that bone marrow macrophages can support norovirus replication when deficient for STAT-1 or an interferon-αβ receptor.

EXAMPLE 17

This example illustrates that MNV-1 productively infects established macrophage cell lines including a human-murine fusion cell line.

Figure 6:
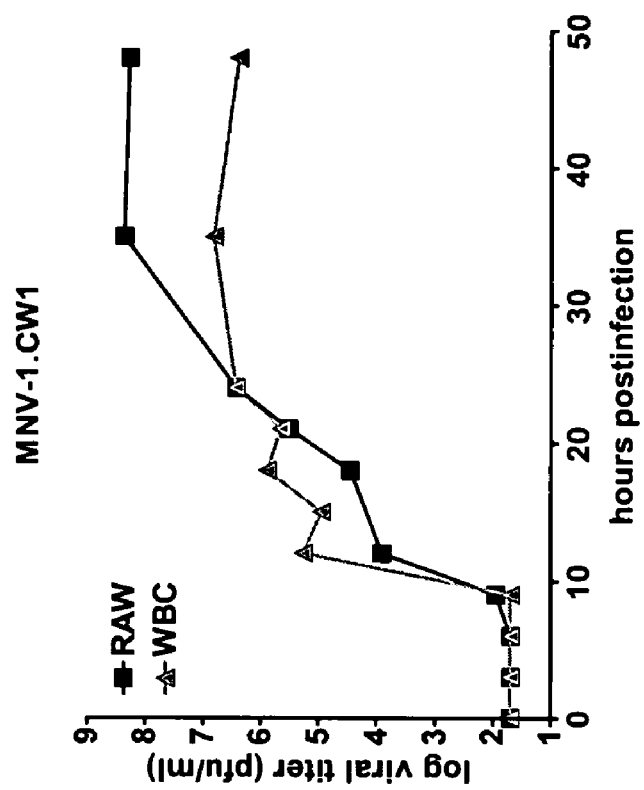
Figure 6:
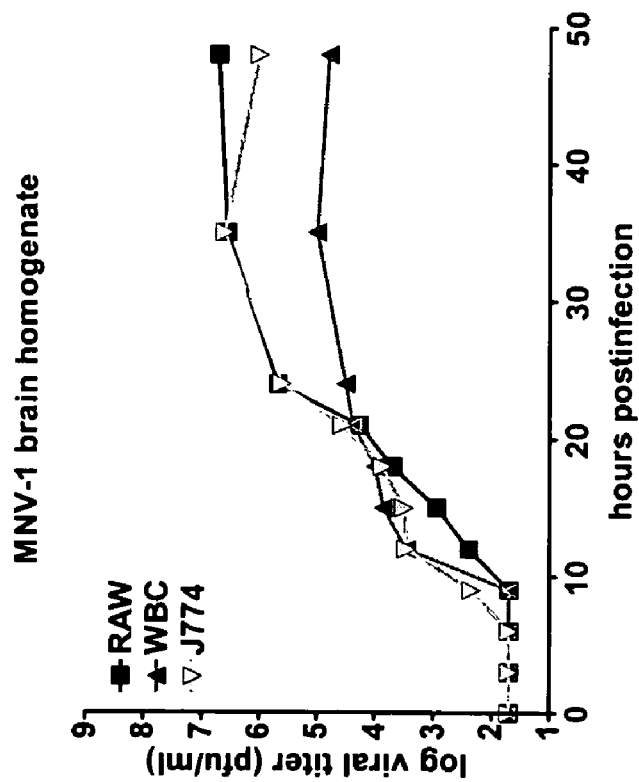

In this example, as shown in FIG. 6, RAW 264.7, J774A.1 and WBC264-9C cells (a human leukocyte/murine macrophage hybrid, ATCC catalog number HB-8902) were examined for their permissiveness towards norovirus infection. In these experiments, the cells were infected as described in example 12 with an MOI of 0.05 with MNV-1 containing brain homogenate or plaque-purified MNV-1.CW1. Cells were subjected to freezing and thawing at various time intervals after infection. Virus production was measured by titering using the plaque assay described in Example 3. The data in FIG. 6 are from a single experiment. The data indicate that MNV-1 productively infects each of these macrophage cell lines.

EXAMPLE 18

This example illustrates a consensus sequence of a murine norovirus.

This sequence, set forth as SEQ ID NO: 1, consists of 7382 nucleotides of a single stranded (positive strand) RNA molecule which can serve as a murine norovirus genome.

EXAMPLE 19

This example illustrates a screen for an anti-viral compound.

In this example, a candidate anti-viral compound is added to a culture comprising RAW cells inoculated with MNV-1. Twelve hours after infection, a plaque assay as described in Example 3 is performed on virus released by the culture. A reduction in the number of plaques formed in the plaque assay, compared to the number of plaques formed in a plaque assay on a control culture in which the candidate anti-viral compound was not added, indicates that the candidate compound has anti-viral activity. Further investigation can indicate the viral protein or stage of viral life cycle targeted by the candidate anti-viral compound.

EXAMPLE 20

This example illustrates a screen for an anti-viral compound.

In this example, a candidate anti-viral compound is added to a culture comprising RAW cells inoculated with MNV-1. Eight hours after infection, cells are harvested and lysed, and lysate samples are applied to wells of an ELISA plate. ELISAs are performed on the lysate samples using, for primary antibodies, mouse monoclonal antibodies directed against norovirus polyprotein protease, norovirus RNA polymerase, norovirus VPG, norovirus NTPase or norovirus capsid protein (such as monoclonal antibody MAb A6.2 illustrated in Example 13 and FIG. 2). Antibody binding is revealed using a goat anti-mouse secondary antibody conjugated with horseradish peroxidase and a chromogenic HRP substrate. Signal is quantified by measuring light absorbance using an ELISA plate reader. A reduction in the light absorbance of an ELISA well probed with an antibody compared to the light absorbance of a well coated with lysate from a parallel control sample in which the candidate anti-viral compound was not added, indicates that the candidate compound caused a reduction in accumulation of the antibody's target antigen. This observation indicates that the candidate molecule merits further investigation as an anti-viral compound directed against the accumulation of the target antigen.

All references cited in this specification are hereby incorporated by reference in their entireties. Any discussion of references cited herein is intended merely to summarize the assertions made by their authors and no admission is made that any reference or portion thereof constitutes relevant prior art. Applicants reserve the right to challenge the accuracy and pertinency of the cited references.

The norovirus described above assigned ATCC Accession Number PTA-5935 is on deposit under the terms of the Budapest Treaty with the American Type Culture Collection, 10801 University Boulevard, Manassas, Va. 20110-2209. The strain was deposited on Apr. 27, 2004 and the requisite fees paid. The accession number indicated was assigned after successful viability testing. Access to the culture will be available during pendency of the patent application to one determined by the Commissioner to be entitled thereto under 37 C.F.R. § 1.14 and 35 U.S.C. § 122. All restriction on availability of said culture to the public will be irrevocably removed upon the granting of a patent based upon the application. Moreover, the designated deposit will be maintained for a period of thirty (30) years from the date of deposit, or for five (5) years after the last request for the deposit, or for the enforceable life of the U.S. patent, whichever is longer. Should a culture become nonviable or be inadvertently destroyed, or, in the case of plasmid-containing strains, lose its plasmid, it will be replaced with a viable culture. The deposited material mentioned herein is intended for convenience only, and is not required to practice the present invention in view of the description herein, and in addition, this material is incorporated herein by reference.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A norovirus-permissive cell culture infected with a norovirus, the norovirus-permissive cell culture comprising a macrophage infected with a norovirus, wherein the macrophage is deficient in a cellular anti-viral pathway, the anti-viral pathway selected from the group consisting of a STAT-1-dependent anti-viral pathway, an interferon receptor-dependent anti-viral pathway, a double-stranded RNA-dependent serine/threonine protein kinase-dependent anti-viral pathway, and a combination thereof.

2. A norovirus-permissive cell culture according to claim 1, wherein the macrophages deficient in the STAT-1-dependent anti-viral pathway are STAT-1-deficient macrophages.

3. A norovirus-permissive cell culture according to claim 1, wherein the macrophages deficient in an interferon receptor-dependent pathway are macrophages deficient in an interferon receptor, the receptor selected from the group consisting of an interferon-αβ receptor, an interferon-γ receptor, an interferon λ receptor and a combination thereof.

4. A norovirus-permissive cell culture according to claim 1, wherein the macrophages deficient in an interferon receptor-dependent pathway are macrophages deficient in an interferon receptor, the receptor selected from the group consisting of an interferon-αβ receptor, an interferon-γ receptor and a combination thereof.

5. A norovirus-permissive cell culture according to claim 1, wherein the macrophages deficient in the double-stranded RNA-dependent serine/threonine protein kinase anti-viral-dependent pathway are macrophages deficient in double-stranded RNA-dependent serine/threonine protein kinase.

6. A norovirus-permissive cell culture according to claim 5, wherein the macrophages are selected from the group consisting of RAW 264.7 cells, J774A.1 cells and WBC264-9C cells.

7. A method of replicating a norovirus in vitro, the method comprising:
  inoculating macrophages with the norovirus; and
  culturing the macrophages, wherein the macrophages are macrophages deficient in a cellular anti-viral pathway selected from the group consisting of a STAT-1-dependent anti-viral pathway, an interferon receptor-dependent anti-viral pathway, a double-stranded RNA-dependent serine/threonine protein kinase-dependent anti-viral pathway, and a combination thereof.

8. A method according to claim 7, wherein the macrophages deficient in the STAT-1-dependent anti-viral pathway are STAT-1-deficient macrophages.

9. A method according to claim 7, wherein the macrophages deficient in the interferon receptor-dependent pathway are macrophages deficient in an interferon receptor selected from the group consisting of an interferon-$\alpha\beta$ receptor, an interferon-$\gamma$ receptor, an interferon $\lambda$ receptor and a combination thereof.

10. A method according to claim 7, wherein the macrophages deficient in the double-stranded RNA-dependent serine/threonine protein kinase pathway are double-stranded RNA-dependent serine/threonine protein kinase-deficient macrophages.

11. A method according to claim 7, wherein the macrophages are selected from the group consisting of RAW 264.7 cells, J774A.1 cells and WBC264-9C cells.

12. A norovirus-permissive cell culture infected with a norovirus, wherein the norovirus-permissive cell culture comprises dendritic cells.

13. A method of replicating a norovirus in vitro, the method comprising:
  inoculating dendritic cells with the norovirus; and
  culturing the dendritic cells.

14. A method according to claim 13, wherein inoculating the dendritic cells with the norovirus comprises infecting the dendritic cells with the norovirus.

* * * * *

SEQUENCE LISTING

<160> NUMBER OF SEQ ID NOS: 1

<210> SEQ ID NO 1
<211> LENGTH: 7382
<212> TYPE: RNA
<213> ORGANISM: Mouse norovirus

<400> SEQUENCE: 1
gugaauucua gaaggcaacg ccaucuucug cgcccucugu gcgcaacaca gagaaacgca 60
aaaacaagaa ggcuucgycu aaagcuagug ucuccuuugg agcaccuagc ccccucucuu 120
cggagagcga agacgaaruu aauuacauga ccccuccuga gcaggaagcu cagcccggcg 180
cccuugcggc ccuucaugcg gaagggccgc uugccgggcu ccccgugacg cguagugaug 240
cacgcgugcu gaucuucaau gagugggagg agaggaagaa gucugauccg uggcuacggc 300
uggacauguc ugauaaggcu aucuuccgcc guuaccccca ucugcggccu aaggaggaua 360
ggccugacgc gcccucccau gcggaggacg cuauggaugc caaggagccu gugaucggcu 420
cuaucuugga gcaggaugau cacaaguuuu accauuacuc ugucuacauc gguggcggcc 480
uugugauggg ggucaacaac cccagugcug cggucugcca ggcaacgauu gauguggaga 540
agcuacaccu cugguggcgg ccugucuggg agccccgcca wccccuugac ucggcugagu 600
ugaggaagug cgugggcaug acuguccccu acguggccac caccgucaac uguuaucagg 660
ucugcugcug gauuguuggc aucaaggaca ccuggcugaa gagggcgaag aucucuagag 720
aucugcccuu cuacagcccc guccaggacu ggaacgucga cccccaggag cccuucauuc 780
cauccaagcu caggaugguc ucggauggca uccugguggc cuugucggca gugauuggcc 840
ggccaauuaa gaaccuacug gccucaguua agccgcucaa cauucucaac aucgugcuga 900
gcugugauug gaccuuuucg ggcauuguca augcccugau cuugcuugcu gagcucuuug 960
acaucuuuug gacccccccu gauguracca rcuggaugau cucuaucuuc ggggaauggc 1020
aggccgaagg gcccuucgac cyugcucuug acguggugcc cacccuguug ggcgggaucg 1080
ggauggcuuu uggccucrcc ucugagacca ucgggcgcaa gcucdcuucc accaacucgg 1140
cucucaaggc cgcccaagag augggcaagu ucgccauaga ggucuucaag caaauuaugg 1200

```
ccuggaucug gcccucugag gacccagugc cagcccucuu auccaacaug gagcaggcca    1260
ucauuaagaa ugagugucaa cudgagaacc aacucacggc cauguugcgg gaucgcaacg    1320
caggggcuga auuccuvagg ucccuugaug aggaggagca ggaaguccgc aagaucgcag    1380
cuaagugcgg caacucggcc accacuggaa ccaccaacgc ucugcuggcc aggaucagca    1440
uggcccgcgc ggccuuugag aaagcucgcg cugaacagac cucccgaguc cgcccugugg    1500
ugducauggu cucaggcagg cccgggaucg ggaaaaccug cuuuugccaa aaccuagcca    1560
agaggauugc ugcgucccug ggugaugaga ccucuguugg caucauacca cgcgcugaug    1620
ucgaccacug ggaugcuuac aagggagcca gagugguucu cugggaugau ucggcaugg    1680 acaacguggu gaaggaugca cugaggcuuc agaugcuugc cgacacgugc ccagugacac    1740
ucaauuguga caggauugag aacaaggaa agaugyuuga cucucagguc auuaucauca    1800
ccacaaauca acaaaccccc gygcccugg acuaugucaa ccuggaggcg gucugccgcc    1860
gcauagauuu ccugguuuau gmugagagcc cuguuguuga ugaugcucgg gccagagccc    1920
cuggcgaugu gaaugcagug aaagcugcca ugaggcccga uuacagccac aucaauuuca    1980
ucuuggcacc gcagggcggc uuugaccguc gggaaacacc cccuacggua agggcgucac    2040
caagaucauu ggcgccacug cucuuugcgc gagagcgguu gcucuugucc augagcgcca    2100
ugaugauuuc ggccuccaga acaaggucya ugacuuugau gcgcgcaarg ucaccgccuu    2160
caaagccaug gcggcugacg ccggcauucc augguacaaa auggcagcua uugggugcaa    2220
agcaaugggg gugcaccugu guagaggagg ccaugcauuu acuuaaggau uaugaggugg    2280
cucccuguca ggugaucuac aauggugcca ccuauaaugu gagcugcauc aagggugccc    2340
caaugguuga aaaggucaag gagccugaau ugcccaaaac acuugucaac uguguucagaa    2400 ggauaaagga ggcccgccuc cgcugcuacu guaggauggc ugcugacguc aucacgucca    2460
uucugcaggc ggccggcacg gccuucucua uuuaccacca gauugagaag ggucuagac    2520 cauccuuuua uugggaucau ggauacaccu accgugacgg accuggaucc uuugacaucu    2580
uugaggauga cgaugauggg ugguaccacu cugagggaaa gaagggcaag aacaagaagg    2640 gccggggggcg acccggaguc uucagaaccc guggggcucac ggaugaggag uacgaugaau    2700
ucaagaagcg ccgcgagucu aggggcggca aguacccau ugaugauuac cucgcugrcc    2760
gcgagcgaga agaagaacuc cuggagcggg acgaggagga ggcuaucuuc ggggayggcu    2820
ucggguugaa ggccaccgc cguucccgca aggcagagag agccaaacug ggccugguuu    2880
cugguggcga cauccgcgcc cgcaagccga ucgacggaa uguggauggc cccuccuggg    2940
cugacgauga ccgccaagguc gcuacggcga aagaucaac uuugagggccc caguyccau    3000 cuggucccgu guugugcagu ucggcacggg guggggcuuu uggggugagc ggccacgucu    3060
ucaucaccgc caagcaugug gcgcccccca agggcacgga gaucuuuggg cgcaagcccg    3120
gggacuucac ugucrcuucc agcggggacu ucuugaagua cuacuuaccc agcgccguca    3180
ggccugacru ucccgccaug guccuggaga augggugcca ggaggcgguc gucgccucgg    3240
uccuugucaa gagagccucc ggcgagaugc uugcccuggc ugucaggaug gguucacagg    3300
ccgccaucaa gauugguagu gccguugugc augggcaaac uggcaugcuc cugacuggcu    3360
cuaaugccaa ggcccaggac cucggggcca ucccgggcga cuguggcugu cccuauguuu    3420
auaagaaggg uaacaccugg guugugauug gggugcacgu ggcggccacu aggucuggua    3480
acacagucau ugccgccacu cacgagaaac ccacacuuga ggcucuggag uuccagggac    3540
cccccaugcu uccccgcccc ucaggcaccu augcaggccu cccaucgcc gauuacggcg    3600
```

```
acgcucccccc cuugagcacc aagaccaugu ucuggcguac cucgccagag aagcuucccc    3660
cuggggcuug ggagccagcc uaucucggcu cuaaagauga gagggguggac gguccuuccc    3720 uucagcaggu caugcgagau cagcuuaagc ccuauucaga accacgcggu cugcuucccc    3780
cucaagaaau ccuugaugca gucugcgacg ccauugagaa ccgccuugag aacacccuug    3840
aaccacagaa gcccuggaca uuuaagaagg cuugugagag cuuggacaag aacaccagya    3900 gygggu auccc cuaucacaag cagaagagca aggacuggac ggggagcgcu uuuauuggcg    3960
rucuugguga ccaggccacc cacgccaaca acauguauga gaugggu aaa uccaugcgac    4020 ccauuuauac agcugcccuc aaggaugaac ugguuaagcc agacaagauc uacgggaaga    4080
uaaagaagag gcuucucugg ggcucugacc uugrcaccau gauucgcgcu gcccgugcyu    4140
uuggcccuuu cugugaugcu cugaaagaar ccugcauuuu caaccccauc agagugggca    4200
ugucgaugaa cgaagauggc cccuucaucu ucgcaagaca cgccaauuuc agguaccaca    4260
uggaugcuga cuauaccagg ugggacucca cccaacagag agccauccua aagcgcgcug    4320
gygacaucau ggygcgccuc uccccugagc cagacuuggc ucggguugc auggaugauc    4380 uccuggcccc cucgcuguug gacgucggcg acuruaagau cguugcgag gaggggcucc    4440 cauccggcug cccuugcacc acacagcuga auaguuuggc ucacuggauu ugacccuuu    4500 gugcaauggu ugagguaacc cgaguugacc cugacauugu gaugcaagaa ucgaguuyu    4560 ccuucuaugg ugaugacgag guggu uucga ccaaccucga guuggauaug guuaaguaca    4620
ccauggcuuu gaggcgguac ggucccuccc cgacucgcgc ggacaaggag gagggaccuc    4680
uggagcgucg ccagacgcug cagggcaucu ccuuccugcg ccgugcgaua uuggugacc    4740 aguuuggggu guacgucgu cuugaucgug ccagcaucga ccgccagcuc cucuggacua    4800
aaggaccuaa ccaccagaac ccc uuugaga cucucccugg acaugcucag agacccuccc    4860
aacuaauggc ccugcucggu gaggcugcca ugcauguga aaaguauuac aggacugugg    4920
cuucccgugu uccaaggag gccgcccaaa gugggauara aauggcuuac cccacgccac    4980
cgaucuguuu ugcgcugggu gcgcuuugga aauggaugc ugagacccg cagggaacgcu    5040 cagcagucuu ugugaaugag gaugagugau ggcgcagcgc caaaagccaa uggcucugag    5100
gccagcggcc aggaucuugu uccugccgcc guugaacagg ccguccccay ucaacccgug    5160
gcuggcgcgg cucuugccgc cccgccgcc gggcaaauua ccaaauugr ccccuggauc    5220 uccaaaauu uugucccagug cccccuuguu gaguuucca uucgccucg aaacacccca    5280 ggugaaauac uguuugauuu ggcccucggg ccagggcuua accccuaccu ugcccaccuc    5340
ucagccaugu acaccggcug gguugggaac ruggagguc agcuggucu cgccggcaau    5400 gccuuuacug cuggcaaggu gguuguugcc cuuguaccac ccuauuuucc caaggggguca    5460 cucaccacug cccagaucac augcuuccca caugucaugu gugaugugcg cacccuggag    5520
cccauucaac uccucuuucu ugaugugcgu cgaguccuuu ggcaugcuac ccaggaucaa    5580
gaggaaucua ugcgccuggu uugcaugcug uacgccac uccgcacaaa cagcccgggu    5640
gaugagucuu uuguggucuc uggccgccuu cuuucuaagc cggcggcuga uuucaauuuu    5700
gucuaccuaa cucccccau agagagaacc aucuaccgga uggucgacuu gcccgugaua    5760
cagccgcggc ugugcacgca cgcacguugg ccugccccgg ucuauggucu cuugguggac    5820
ccaucccucc ccucaaauucc ccaguggcag aauggaaggg ugcacguuga uggaccccug    5880
cuugguacca ccccaaucuc cgguucaugg gugccugcu uugcgkcgga ggcugccuau    5940
```

-continued

```
aaguuccaau cgggcaccgg ugagguggcg acauucaccc ugauugagca ggauggaucu    6000
gccuacgucc ccggugacag ggcagcacca cucggguuac cccgauuucu cugggcaacu    6060
ggagaucgag guccagaccg agaccaccaa gacuggagac aagcucaagg ucaccacuuu    6120
gagaugauuc uuggcccaac gaccaacgcg gaccaggccc ccuaccaggg cagguguuc     6180 gccagcguca cugcugcggc cucucuugac uuggug gaug gcagggu ucg ug cggu ccca 6240 agauccaucu acguuuuca ggacaccauc ccugaauaca acgaugggcu acugguuccc    6300 cuugccccc caauuggucc cuuucucccc ggcgaggucc uccugagguu ccggaccuac     6360
augcgucaga ucgacaccgc ugacgccgca gcagaggcga uagacugugc acuccccag    6420 gaguuugucu ccugguucgc gucuaacgcg uucaccgugc aguccgaggc ccugcuccuu    6480
agauacagga acaccugac ugggcaacug cuguucgagu gcaagcucua caacgaaggu    6540
uacaucgccu ugucuuauuc cggcucagga cccucaccu ucccgaccga uggcaucuuu     6600
gaggucguca guugggguucc ucgccuuuac caauuggccu cugugggaag uuuggcaaca    6660
ggccgaaugc ucaaacaaua auggcuggug cucuuuugg agcgauugga gguggccuga     6720
ugggcauaau uggcaauucc aucucaaaug uucaaaaccu ucaggcaaac aaacaauugg    6780
cagcucagca auuugguuau aauucuuccc ugcuugcaac gcaaauucaa gcccagaagg    6840
aucucacucu gauggggcag caauucaacc agcagcucca aaccaacucu uucaagcacg    6900
acuuggaaau gcuuggcgcu caggugcaag cccaggcgca ggcccaggag aacgccauca    6960
auaucaaaac ggcgcagcuc caggccgcag gcuuuucaaa gacagaugcc acacgccuug    7020
ccuuggggca gcagcccacg agggccgugg auuggucugg gacgcgguac uacaccgcua    7080
accagccagu cacgggcuuc ucggguggcu uuaccccaac cuacacucca gguaggcaag    7140
ugacaucccg cccugug gac acaucccuc uaccgaucuc gggug gacgc uugcccuccc   7200 uucguggagg uuccuggucc ccgcgcgacc auacgccggc gacucaaggc accuacacga    7260
acggacgguu cgugucucuc ccuaagaucg ggaguagcag ggcauaggu u ggaagagaaa    7320 ccuuuuguga aaaugauuuc ugcuuacugc uuucuuuucu uugugguagu uagaugcauu    7380
uc                                                                  7382
```